(12) United States Patent
Li et al.

(10) Patent No.: US 8,631,714 B2
(45) Date of Patent: Jan. 21, 2014

(54) MULTIFUNCTIONAL SPECIMEN BOX

(75) Inventors: Xianglong Li, Shanghai (CN); Zhong Wang, Shanghai (CN); Qin Wang, Shanghai (CN)

(73) Assignee: Suzhou Halo Bio-Tech Co., Ltd., Suzhou, Jiangsu Province (CN)

(*) Notice: Subject to any disclaimer, the term of this patent is extended or adjusted under 35 U.S.C. 154(b) by 182 days.

(21) Appl. No.: 13/387,732

(22) PCT Filed: Jun. 3, 2010

(86) PCT No.: PCT/CN2010/073492
§ 371 (c)(1),
(2), (4) Date: Jan. 28, 2012

(87) PCT Pub. No.: WO2011/012020
PCT Pub. Date: Feb. 3, 2011

(65) Prior Publication Data
US 2012/0125125 A1   May 24, 2012

(30) Foreign Application Priority Data
Jul. 30, 2009 (CN) ...................... 2009 2 0075562 U

(51) Int. Cl.
*G01N 1/38* (2006.01)
(52) U.S. Cl.
USPC ..................................... 73/863.23; 73/864.91

(58) Field of Classification Search
USPC ........................................ 73/863.23, 864.51
See application file for complete search history.

(56) References Cited

U.S. PATENT DOCUMENTS 5,431,884 A * 7/1995 McDonough et al. ........ 422/534

FOREIGN PATENT DOCUMENTS

KR          760675 B1 * 9/2007
WO PCT/CN2010/073492    9/2010

* cited by examiner

*Primary Examiner* — Hezron E Williams
*Assistant Examiner* — Paul West
(74) *Attorney, Agent, or Firm* — Global IP Services; Tianhua Gu

(57) ABSTRACT

A modified multi-function specimen box is provided. The modified multi-function specimen box includes a box body (1). A box cover (2) is disposed on an opening of the box body (1). A fixed rotary spindle (4) is disposed on the box cover (2). The fixed rotary spindle (4) is capable of freely rotating with respect to the box cover (2). A sampling spoon (5) is disposed at the bottom of the fixed rotary spindle (4). A filter screen (3) is disposed in an inner cavity of the box body (1) in a direction perpendicular to the box cover (2), and the filter screen (3) divides the box body (1) into a liquid addition cavity (11) and a liquid suction cavity (12). The present invention achieves the dilution, uniform mixing, and filtration of a specimen.

8 Claims, 2 Drawing Sheets

MULTIFUNCTIONAL SPECIMEN BOX

CROSS REFERENCE TO RELATED PATENT APPLICATION

The present application is the US national stage of PCT/CN2010/073492 filed on Jun. 3, 2010, which claims the priority of the Chinese patent application No. 200920075562.7 filed on Jul. 30, 2009, which application is incorporated herein by reference.

FIELD OF INVENTION

The present invention relates to a medical test container, and specifically to a modified multi-function specimen box.

BACKGROUND OF THE INVENTION

Among the three main routine tests done for patients in a hospital, stool routine test (physical microscopic examination) is an essential item. In addition to the necessary stool routine test done for the patients, some necessary chemical tests (e.g. fecal occult blood test) for stool specimens of the patients are also performed according to the difference of the conditions of the patients, so as to make an accurate diagnosis for patients. At present, in the physical and chemical tests for stool, steps starting from specimen collection to specimen treatment at the end of the test are as follows. A patient dips a stool specimen into a box, a plastic bag, or a paper bag by using a cotton swab or other objects, and then delivers the specimen with a test sheet to a laboratory. A laboratory technician smears the stool specimen and carries out physical microscopic examination according to the requirements of test items on the test sheet, prepares some stool specimen dilutions for chemical test, and performs special disinfection and treatments on apparatus accommodating the stool specimen and other articles after test, so as to prevent nosocomial infection and laboratory pollution. However, air in the laboratory is polluted by the off odour of the specimen since the operations and tests are carried out in an open space.

SUMMARY OF THE INVENTION

In view of the above technical problems, the present invention is directed to a modified multi-function specimen box having a liquid addition, agitation, and filtering function.

In order to solve the above technical problems, a modified multi-function specimen box of the present invention includes a box body. A box cover is disposed on an opening of the box body. A fixed rotary spindle is disposed on the box cover. The fixed rotary spindle can freely rotate with respect to the box cover. A sampling spoon is disposed at the bottom of the fixed rotary spindle. A filter screen is disposed in an inner cavity of the box body in a direction perpendicular to the box cover, and the filter screen divides the box body into a liquid addition cavity and a liquid suction cavity.

Preferably, a swivel mouthpiece is disposed on the top of fixed rotary spindle.

In addition, the swivel mouthpiece is of a taper shape.

Preferably, the box cover is tightly connected to the box body.

Preferably, an insertion hole is disposed on the box cover. The insertion hole is sealed with self-adhesive paper, and the insertion hole is located above the liquid suction cavity. The fixed rotary spindle is located in the liquid addition cavity.

Preferably, the filter screen is an asymmetric membrane permitting only one-way penetration.

In addition, a liquid addition needle is further disposed on the box cover, and the liquid addition needle and the fixed rotary spindle are both located in the liquid addition cavity.

A specimen box of the present invention includes a box body, a box cover is disposed on an opening of the box body, a fixed rotary spindle is disposed on the box cover, the fixed rotary spindle can freely rotate with respect to the box cover, a sampling spoon is disposed at the bottom of the fixed rotary spindle, a filter screen is disposed in an inner cavity of the box body in a direction perpendicular to the box cover, a spacer is connected to the bottom of the filter screen, and the filter screen and the spacer divide the box body into a liquid addition cavity and a liquid suction cavity.

In use of the specimen box of the present invention, a sampler opens the box cover first. At this time, the box cover serves as a handle of the sampling spoon. A suitable amount of specimen is taken by using the sampling spoon. The specimen box is tightly covered with the box cover, and then delivered to an operation room. Then, the modified multi-function specimen box is fixed on a rack of the modified multi-function specimen box. A diluent is added by the liquid addition needle, and the swivel mouthpiece is connected to a swivel joint. The sampling spoon rotates with the fixed rotary spindle. In this case, the sampling spoon serves as an agitating blade, so as to achieve the uniform mixing function of the modified multi-function specimen box. Because the box body of modified multi-function specimen box is made from a transparent material, the color and traits of the specimen can be observed in agitation. Subsequently, impurities of big particles in the diluted and uniformly mixed liquid are trapped by the filter screen when passing through the filter screen, so as to prevent the impurities of big particles from occluding a pipe of a tester.

Numeral list of accompanying drawings:

| | | | |
|---|---|---|---|
| 1. | Box body | 3. | Filter screen or asymmetric membrane |
| 11. | Liquid addition cavity | 4. | Fixed rotary spindle |
| 12. | Liquid suction cavity | 41. | Swivel mouthpiece |
| 2. | Box cover | 5. | Sampling spoon |
| 21. | Insertion hole | 6. | Liquid addition needle |
| 22. | Self-adhesive paper | 7. | Spacer |

DETAIL DESCRIPTION OF THE PREFERRED EMBODIMENTS

The modified multi-function specimen box of the present invention is described in detail below with reference to accompanying drawings.

The specimen box of the present invention is applicable to the test of medical specimen, and especially stool specimen.

Embodiment 1

Figure 1:
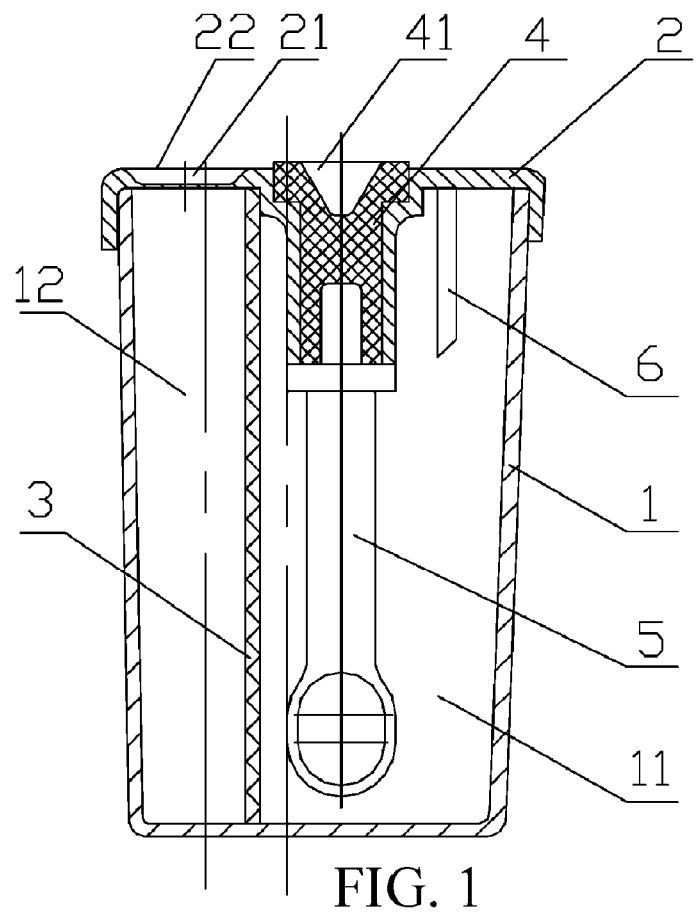
FIG. 1 is a structural diagram of a first embodiment of the present invention.

As shown in FIG. 1, a specimen box of the present invention includes a flat-bottom box body 1, a box cover 2 mated with the box body 1 is disposed on an opening of the box body 1, a through insertion hole 21 is cut on the box cover 2, and a fixed rotary spindle 4 and a liquid addition needle 6 are disposed on the box cover 2. The fixed rotary spindle 4 and the box cover 2 are clearance fitted, and the fixed rotary spindle 4 can freely rotate with respect to the box cover 2. Tight connection is required between the box cover 2 and the box body 1, and between the liquid addition needle 6 and the box cover 2.

A filter screen 3 is disposed in an inner cavity of the box body 1, the filter screen 3 is disposed in perpendicular to the box cover 2, and periphery of the filter screen 3 is tightly connected to the box body 1 and the box cover 2. The filter screen 3 divides the box body 1 into a liquid addition cavity 11 and a liquid suction cavity 12.

Figure 2:
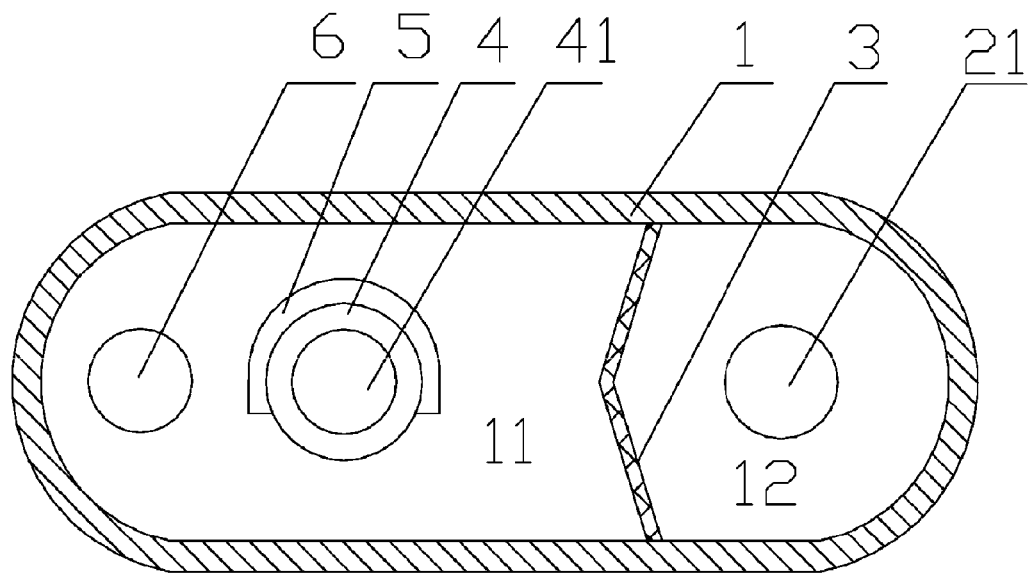
FIG. 2 is a top view of the present invention.

The filter screen 3 is preferably an asymmetric membrane 3. Cells, insect eggs, and other materials in a medical specimen can only penetrate from one side of the asymmetric membrane 3 to the other side of the one-way osmosis membrane, and cannot penetrate reversely. Impurities of big particles in the medical specimen cannot pass through the asymmetric membrane 3. The asymmetric membrane 3 may be commercially available. A cross section of the asymmetric membrane 3 is folding ruler like, as shown in FIG. 2, and such a shape can be easily fabricated with a low cost.

A liquid suction needle is located in the liquid suction cavity 12 at one side of the asymmetric membrane 3, and a sampling spoon 5 and the liquid addition needle 6 are located in the liquid addition cavity 11 at the other side of the asymmetric membrane 3.

An upper part of the fixed rotary spindle 4 is T shaped, so that the fixed rotary spindle 4 will not fall in the box body 1 under the action of gravity. A swivel mouthpiece 41 with an opening facing upward is disposed on the top of fixed rotary spindle 4, and the swivel mouthpiece 41 is of a tape shape, as shown in FIGS. 1 and 2.

The sampling spoon 5 is disposed at the bottom of the fixed rotary spindle 4. The sampling spoon 5 is of a spoon shape.

The box body 1 is made from a transparent material, and the fixed rotary spindle 4 is made from an opaque plastic. The box cover 2 is made from a transparent plastic.

In order to ensure that the specimen in the box body 1 does not volatize and pollute ambient environment after the specimen is sampled, and before the specimen is delivered to a testing room, self-adhesive paper 22 is stuck to the insertion hole 21. The self-adhesive paper 22 exerts a sealing effect, can effectively prevent the diffusion of off odour from the specimen, facilitates the successful insertion of the liquid suction needle of a tester into the specimen box as the self-adhesive paper 22 is soft, and also can be used to wipe the liquid suction needle when the liquid suction needle exits the specimen box.

In use of the specimen box of present invention, the operation steps are as follows.

First, a sampler opens the box cover 2, at this time, the box cover 2 serves as a handle of the sampling spoon 5, a suitable amount of specimen is taken by using the sampling spoon 5, and then the specimen box is tightly covered with the box cover 2, and then delivered to an operation room.

Then, the liquid suction needle of the tester used in combination with the specimen box of present invention perforates the self-adhesive paper 22 sealed on the insertion hole 21, and is inserted into the box body 1. The liquid suction needle is located in the liquid suction cavity 12 at one side of the asymmetric membrane 3, and the sampling spoon 5 and the liquid addition needle 6 are located in the liquid addition cavity at the other side of the asymmetric membrane 3.

Afterwards, a suitable amount of diluent is added to the box body 1 by the liquid addition needle 6. A regular swivel joint of the tester is press fitted to the swivel mouthpiece 41 on the top of the fixed rotary spindle 4, so that the fixed rotary spindle 4 is driven to rotate by a frictional force between the regular swivel joint and the swivel mouthpiece 41, and the sampling spoon 5 rotates with the fixed rotary spindle 4, thereby diluting and uniformly mixing the specimen. After the specimen is diluted and uniformly mixed, impurities of big particles cannot pass through the asymmetric membrane 3, and are trapped in the liquid addition cavity 11, so that the impurities of big particles will not enter the liquid suction needle, thereby preventing the occlusion of a pipe of the tester. Cells, insect eggs, and other materials can pass through the asymmetric membrane 3, and reach the liquid suction cavity 12 at the side of the liquid suction needle. According to the property of the asymmetric membrane 3 that reverse osmosis is not allowed, the cells, insect eggs, and other materials cannot reversely penetrate back to the liquid addition cavity 11, and thus the disposition of the asymmetric membrane 3 can increase the concentration of the specimen solution in the liquid suction cavity 12, and improve the test sensitivity.

Finally, based on different pipes, the tester suctions the specimen under vacuum by using the liquid suction needle, so as to suction the diluted and uniformly mixed specimen into the liquid suction needle, and then transfer the suctioned specimen solution to a counting chamber for test. Alternatively, the specimen solution is suctioned by different pipes into a chemical testing room for corresponding chemical test.

For the modified multi-function specimen box, the sampling, diluting, uniform mixing, and testing of the specimen are all carried out in the modified multi-function specimen box, which is of great advantage compared with the original stool specimen collection, standing, and final specimen disinfection. Therefore, the modified multi-function specimen box can be simply and conveniently operated, and can effectively prevent the adverse effect caused by unsuitable treatment and disinfection of the stool specimen.

The modified multi-function specimen box solves the problem of laboratory pollution caused in the process starting from the collection of the specimen to the physical and chemical test operations and the final treatment of the specimen in the specimen test in the prior art, and can effectively prevent the nosocomial infection caused by unsuitable treatment of the stool specimen.

The disposition of the asymmetric membrane 3 not only achieves the function of the filter screen 3, but also increases the concentration of materials to be tested such as cells and insect eggs in the specimen solution, thereby improving the test sensitivity.

Embodiment 2

Figure 3:
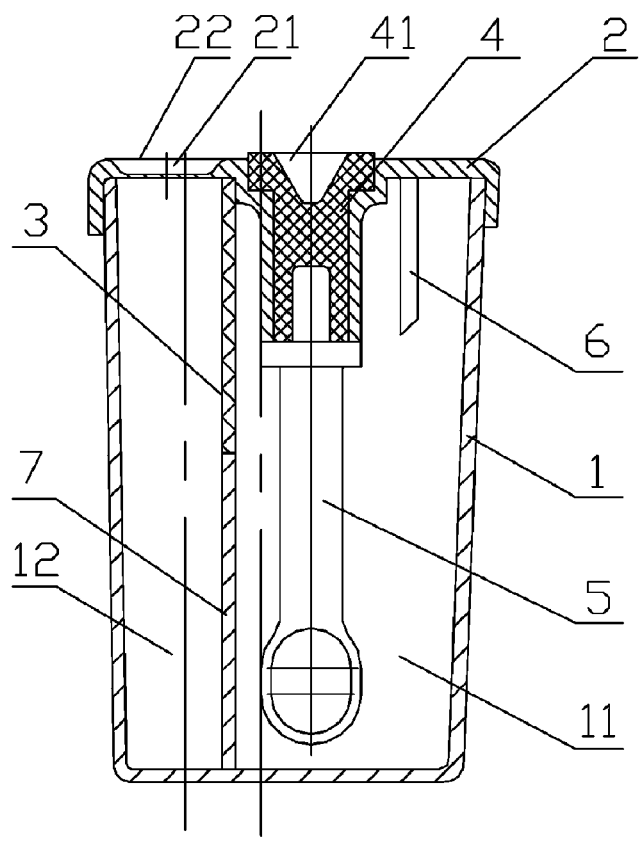
FIG. 3 is a structural diagram of a second embodiment of the present invention.

This embodiment is different from Embodiment 1 by the disposition of the filter screen 3. In Embodiment 1, the top of the filter screen 3 is connected to the box cover 2, and the bottom is connected to the bottom of the box body 1. In Embodiment 2, a spacer 7 is disposed below the filter screen 3, to block the communication of diluent at two sides of the filter screen 3, as shown in FIG. 3. The bottom of the filter screen 3 is connected to the top of the spacer 7, and the box body 1 is thus divided into a left and a right part, which are respectively the liquid addition cavity 11 and the liquid suction cavity 12. Other technical features of Embodiment 2 are the same as those in Embodiment 1.

Liquid addition in Embodiment 2 is achieved through two times of addition. After the specimen is added by using the sampling spoon 5, the diluent is added to a level below the filter screen 3, and the fixed rotary spindle is rotated to drive the sampling spoon 5 to rotate, so as to agitate and uniformly mix the specimen solution in the box body 1. After the specimen solution is agitated and uniformly mixed, the diluent is added for a second time. The diluent is added slowly with agitation, to a suitable level of the filter screen 3 that is above the spacer 7. In this way, the uniform mixing and filtration of the specimen solution are achieved.

The disposition of the spacer 7 below the filter screen 3 has the advantage that because the rate at which the diluent pass through the filter screen 3 is far greater than the diffusion rate of visible components such as cells and insect eggs, in Embodiment 1, after the diluent is added to the box body 1, a certain period of time is required before the specimen is uniformly mixed through agitation. In this period of time, the diluent quickly passes through the filter screen 3 and reaches the liquid addition cavity 11 at the other side of the filter screen 3. In embodiment 2, the spacer 7 is disposed below the filter screen 3, the diluent added at the first time is under the level of the filter screen 3, so the diluent is effectively retained in the liquid addition cavity 11, thus preventing part of the diluent from passing through the filter screen 3 and reaching the liquid suction cavity 11 upon the addition of the diluent. After the fist time of agitation and uniform mixing, the diluent is further added into the liquid addition cavity 11, to a suitable level of the filter screen 3. At this time, the diluent is added with stirring, so that the concentration of the specimen solution in the liquid suction cavity 11 will not be too low, and visible components such as cells and insect eggs can be uniformly distributed in the liquid suction cavity 11 and the liquid addition cavity 11.

The above design examples are provided only for illustration of the present invention, but not intended to limit the scope of the claims. Other essentially equivalent means occurred to those skilled in the art fall in the scope of the claims of the present invention.

What is claimed is:

1. A modified multi-function specimen box, comprising a box body (1), wherein a box cover (2) is disposed on an opening of the box body (1), a fixed rotary spindle (4) is disposed on the box cover (2), the fixed rotary spindle (4) is capable of freely rotating with respect to the box cover (2), a sampling spoon (5) is disposed at the bottom of the fixed rotary spindle (4), a filter screen (3) is disposed in an inner cavity of the box body (1) in a direction perpendicular to the box cover (2), and the filter screen (3) divides the box body (1) into a liquid addition cavity (11) and a liquid suction cavity (12).

2. The modified multi-function specimen box according to claim 1, wherein a swivel mouthpiece (41) is disposed on the top of the fixed rotary spindle (4).

3. The modified multi-function specimen box according to claim 2, wherein the swivel mouthpiece (41) is of a taper shape.

4. The modified multi-function specimen box according to claim 1, wherein the box cover (2) is tightly connected to the box body (1).

5. The modified multi-function specimen box according to claim 1, wherein an insertion hole (21) is disposed on the box cover (2), the insertion hole (21) is sealed with self-adhesive paper (22), the insertion hole (21) is located above the liquid suction cavity (12), and the fixed rotary spindle (4) is located in the liquid addition cavity (11).

6. The modified multi-function specimen box according to claim 1, wherein the filter screen (3) is an asymmetric membrane (3) permitting only one-way penetration.

7. The modified multi-function specimen box according to claim 6, wherein a liquid addition needle (6) is further disposed on the box cover, and the liquid addition needle and the fixed rotary spindle (4) are both located in the liquid addition cavity.

8. A modified multi-function specimen box, comprising a box body (1), wherein a box cover (2) is disposed on an opening of the box body (1), a fixed rotary spindle (4) is disposed on the box cover (2), the fixed rotary spindle (4) is capable of freely rotating with respect to the box cover (2), a sampling spoon (5) is disposed at the bottom of the fixed rotary spindle (4), a filter screen (3) is disposed in an inner cavity of the box body (1) in a direction perpendicular to the box cover (2), a spacer (7) is connected to the bottom of the filter screen (3), and the filter screen (3) and the spacer (7) divide the box body (1) into a liquid addition cavity (11) and a liquid suction cavity (12).

* * * * *